United States Patent
Bean

(10) Patent No.: US 11,957,611 B2
(45) Date of Patent: Apr. 16, 2024

(54) EXTERNAL ANKLE BRACE

(71) Applicant: TayCo Brace, Inc., South Bend, IN (US)

(72) Inventor: Mike W. Bean, South Bend, IN (US)

(73) Assignee: TAYCO BRACE, INC., South Bend, IN (US)

(*) Notice: Subject to any disclaimer, the term of this patent is extended or adjusted under 35 U.S.C. 154(b) by 0 days.

(21) Appl. No.: 17/343,570

(22) Filed: Jun. 9, 2021

(65) Prior Publication Data
US 2021/0298938 A1    Sep. 30, 2021

Related U.S. Application Data

(63) Continuation of application No. 15/074,339, filed on Mar. 18, 2016.

(51) Int. Cl.
*A61F 5/01* (2006.01)

(52) U.S. Cl.
CPC .................. *A61F 5/0127* (2013.01)

(58) Field of Classification Search
CPC ........ A61F 5/0127; A61F 5/01; A61F 5/0102; A61F 5/0195; A61F 5/0111; A61F 5/0113; A61F 5/05841; A61F 5/0585; A61F 5/058; A61F 5/04; A43B 7/20
USPC ........................................ 602/16, 23, 27, 28
See application file for complete search history.

(56) References Cited

U.S. PATENT DOCUMENTS

| | | | |
|---|---|---|---|
| 1,692,896 A | 11/1928 | Hilgert | |
| 4,320,748 A * | 3/1982 | Racette | A61F 5/0585 602/23 |
| 4,510,927 A | 4/1985 | Peters | |
| 4,517,968 A | 5/1985 | Greene et al. | |
| 4,611,414 A | 9/1986 | Vogel | |
| 4,771,768 A | 9/1988 | Crispin | |
| 4,834,078 A | 5/1989 | Biedermann | |
| 5,031,607 A | 7/1991 | Peters | |
| 5,069,202 A | 12/1991 | Prock | |
| 5,094,232 A | 3/1992 | Harris et al. | |
| 5,429,588 A | 7/1995 | Young et al. | |
| 5,454,173 A | 10/1995 | Falguere et al. | |
| 5,571,078 A | 11/1996 | Malewicz | |

(Continued)

OTHER PUBLICATIONS

Merriam-Webster, "monolithic," https://www.merriam-webster.com/dictionary/monolithic.*

(Continued)

*Primary Examiner* — Victoria Hicks Fisher
(74) *Attorney, Agent, or Firm* — Pilloff Passino & Cosenza LLP; Martin J. Cosenza

(57) ABSTRACT

An external ankle brace, including a rigid heel enclosure having a rear portion and a forward portion, wherein the rear portion is for receiving a heel portion of a shoe, the external ankle brace is configured to restrict movement of an ankle in a first direction and permit movement of the ankle in a second direction, wherein the external ankle brace is configured to be disposed on an exterior of the shoe and the shoe having the heel portion, a sole, a toe, a top, and oppositely disposed sides, the forward portion includes a medial sidewall and a lateral sidewall for collectively surrounding the sides of the shoe, the medial and lateral sidewalls being cantilevered from the rear portion of the rigid heel enclosure.

31 Claims, 6 Drawing Sheets

(56) References Cited

U.S. PATENT DOCUMENTS

| | | | |
|---|---|---|---|
| 5,676,642 A * | 10/1997 | Peters | A61F 5/0127 602/23 |
| 5,792,087 A | 8/1998 | Pringle | |
| 5,921,945 A | 7/1999 | Gray | |
| 5,992,057 A | 11/1999 | Monti | |
| 6,053,884 A | 4/2000 | Peters | |
| 6,299,587 B1 * | 10/2001 | Birmingham | A61F 5/0127 602/23 |
| 6,409,695 B1 | 6/2002 | Connelly | |
| 6,669,659 B2 * | 12/2003 | Dittmer | A61F 5/05841 602/16 |
| 6,689,081 B2 | 2/2004 | Bowman | |
| 7,127,836 B1 | 10/2006 | Jamison | |
| 7,624,519 B1 | 12/2009 | Thorne | |
| 7,785,283 B1 | 8/2010 | Bledsoe | |
| 9,259,343 B2 | 2/2016 | Newman | |
| 9,844,455 B2 | 12/2017 | Bradshaw | |
| 2001/0051780 A1 | 12/2001 | Birmingham | |
| 2004/0015112 A1 | 1/2004 | Salutterback et al. | |
| 2004/0034316 A1 | 2/2004 | Castro | |
| 2004/0225241 A1 | 11/2004 | Scheinberg et al. | |
| 2009/0287127 A1 | 11/2009 | Hu et al. | |
| 2010/0137770 A1 | 6/2010 | Ingmundarson et al. | |
| 2011/0173841 A1 | 7/2011 | McDuff | |
| 2012/0145167 A1 | 6/2012 | Davis | |
| 2013/0226059 A1 | 8/2013 | Morris | |
| 2014/0066829 A1 * | 3/2014 | Drillio | A61F 5/0127 602/27 |
| 2015/0088044 A1 | 3/2015 | Walborn et al. | |
| 2015/0216703 A1 | 8/2015 | Madden et al. | |
| 2015/0313743 A1 | 11/2015 | Ostergard | |
| 2016/0029743 A1 | 2/2016 | Cavaliere et al. | |
| 2016/0235578 A1 | 8/2016 | Romo et al. | |
| 2016/0270944 A1 | 9/2016 | Bean | |

OTHER PUBLICATIONS

Martin Alfuth et al., "Biomechanical Comparison of 3 Ankle Braces With and Without Free Rotation in the Sagittal Plane," Journal of Athletic Training, Oct. 2014, pp. 608-616, vol. 49, No. 5.

Patria A. Hume et al., "Effectiveness of External Ankle Support, Bracing and Taping in Rugby Union," Sports Medicine, May 1998, pp. 285-312, vol. 25, No. 5.

The Free Dictionary by Farlex, "Plastically," https://www.thefreedictionary.com/plastically.

* cited by examiner

EXTERNAL ANKLE BRACE

CROSS-REFERENCE TO RELATED APPLICATIONS

This application is a Continuation of U.S. patent application Ser. No. 15/074,339, filed Mar. 18, 2016, naming Mike W. Bean as an inventor, the entire contents of that application being incorporated herein by reference in its entirety.

BACKGROUND

Field

The disclosure pertains generally to preventative and rehabilitative equipment, and more particularly to an ankle brace.

Description of Related Art

In the world of sports, ankle injuries are among the most common cause of lost playing time in a sporting career, with a typical ankle injury leaving the athlete out of competition for up to a month. Ankle sprains occur when there is a rapid shifting of weight from one direction to another. The force generated from the movement causes the foot to roll either inwards, which is known as inversion rotation; or outwards, which is known as eversion rotation. Both the inversion and eversion motion of the ankle cause the ligaments on the outside of the ankle to stretch or tear depending on the force that was generated during the movement.

Current braces vary from woven fabric that acts as a glove and wraps around the ankle, to rigid plastic uprights that are strapped around the ankle. The woven fabric braces typically are made of a thin fabric that envelope the ankle and are laced together to support the ankle from both inversion and eversion rotation. The main drawback with these types of braces is that the material lacks the resistance to prevent the ankle from rolling under intense forces. Further, fabric braces also have to be worn within the shoe, which causes the shoe to fit tighter or, in some cases, forces the user to move up a shoe size in order to wear the brace. In terms of the rigid uprights braces, these braces are typically much heavier than the fabric braces and also much larger. Fitting a rigid brace into a tight shoe almost never works, which forces the user to move up to the next shoe size to accommodate for the bulkiness of the brace. When the user moves up a shoe size, the shoe is no longer sized correctly for the foot and thus loses a portion of its intended use and purpose. These braces leave the user at risk for further injury because either the brace isn't strong enough to support the ankle or the shoe isn't fitted properly to the foot.

SUMMARY

The present device overcomes the disadvantages in the related art in an ankle foot orthotic. The device is an external ankle brace for restricting movement of an ankle in a first direction and permitting movement of the ankle in a second direction, wherein the external ankle brace is disposed on the exterior of a shoe. The shoe has a heel portion, a sole, and oppositely disposed sides. The external ankle brace generally includes a rigid heel enclosure, a lateral upright extension, a medial upright extension, where the upright extensions are pivotally connected to the rigid heel enclosure, and the device lastly includes two fastening systems to secure both sides of the heel enclosure together and to secure the external ankle brace to the shoe. The rigid heel enclosure includes a rear portion and a forward portion. The rear portion is for receiving the heel of the shoe. The forward portion further includes a medial sidewall and a lateral sidewall and is for surrounding the sides of the shoe. The lateral upright extension and the medial upright extension are perpendicular to the rigid heel enclosure and pivotally attached to each respective sidewall. The lower fastening system includes at least one connecting strap for connecting the lateral sidewall to the medial sidewall underneath the sole of the shoe. The upper fastening system includes at least one connecting strap for removably connecting the lateral sidewall to the medial sidewall across the top of the shoe.

The external ankle brace further includes a lateral ankle joint that pivotally connects the lateral upright extension to the lateral sidewall and allows the lateral upright extension to move in the second direction relative to the rigid heel enclosure.

Together, the lateral ankle joint, the lateral upright extension, and the rigid heel enclosure prevent movement of the ankle in the first direction.

Additionally, the external ankle brace further includes a medial ankle joint that pivotally connects the medial upright extension to the medial sidewall and allows the medial upright extension to move in the second direction relative to the rigid heel enclosure.

Together, the medial ankle joint, the medial upright extension, and the rigid heel enclosure prevent movement in the first direction.

Furthermore, the rigid heel enclosure includes oppositely disposed upper and lower ends, where the medial ankle joint is positioned closer to the upper end than the position of the lateral ankle joint.

Lastly, the external ankle brace further comprises an upright fastening system which includes at least one connecting strap for removably connecting the lateral upright extension to the medial upright extension above the ankle.

BRIEF DESCRIPTION OF THE DRAWINGS

These and other features, aspects, and advantages of the present disclosure will become better understood when the following detailed description is read with reference to the accompanying drawings in which like numerals are used to indicate like structure throughout the various figures.

DETAILED DESCRIPTION

Figure 1:
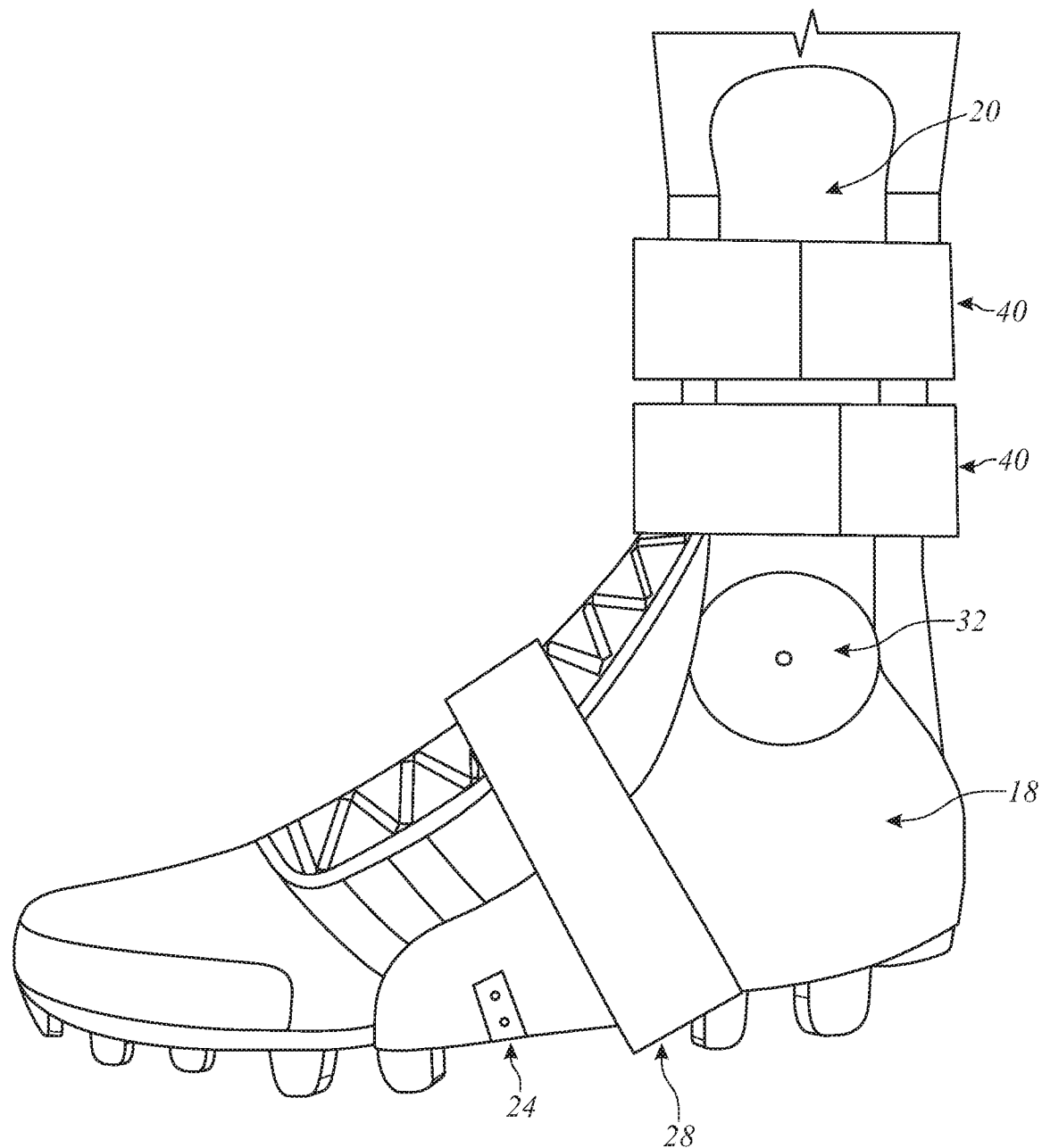
FIG. 1 is a lateral side view showing the external ankle brace with an athletic shoe.

Unless defined otherwise, all technical and scientific terms used herein have the same meaning as is commonly understood by one of skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, the term "and/or" can include any and all combinations of one or more of the associated listed items.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure.

Ankle injuries are among the most common cause of lost playing time in a sporting career and although there are current preventative solutions, those current braces leave the user at risk for further injury because either the brace isn't strong enough to support the ankle or the shoe isn't fitted properly to the foot since "inside the shoe" braces tend to force the user to use a bigger shoe size. The present disclosure provides a rigid support and a much faster application time, all without compromising the fit of the shoe.

The present disclosure relates to an external ankle brace that is adapted to fit around a shoe to prevent and minimize injury to an ankle. The shoe has a heel portion, a sole, and oppositely disposed sides. The interaction between the external ankle brace and the shoe can be seen in FIG. 1.

Figure 2:
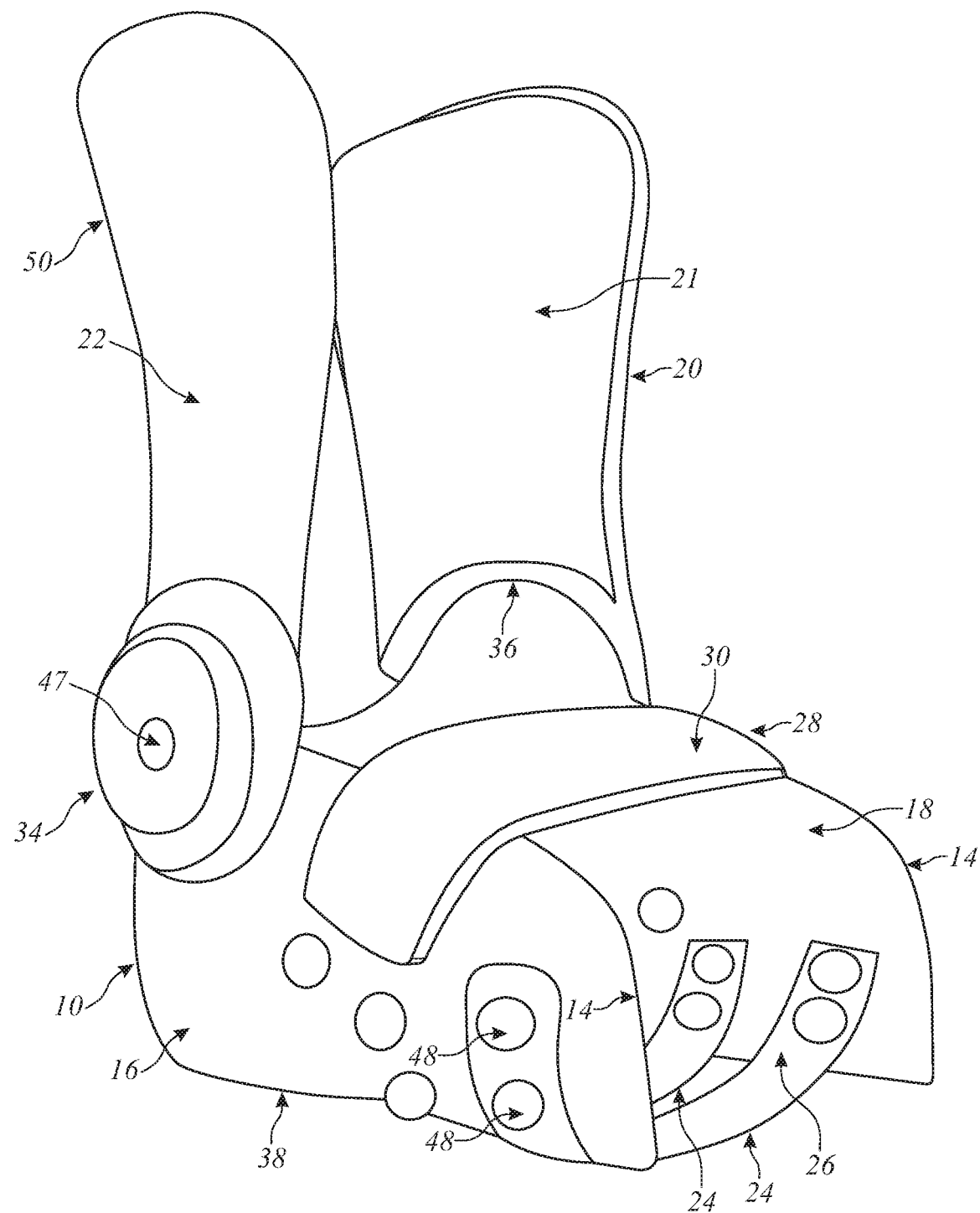
FIG. 2 is a perspective view of the external ankle brace from the medial side.

The external ankle brace of the present disclosure is generally indicated at 50 in FIG. 2. The external ankle brace 50 includes a rigid heel enclosure 10, a lateral upright extension 20, a medial upright extension 22, a lower fastening system 24, and an upper fastening system 28.

Figure 3:
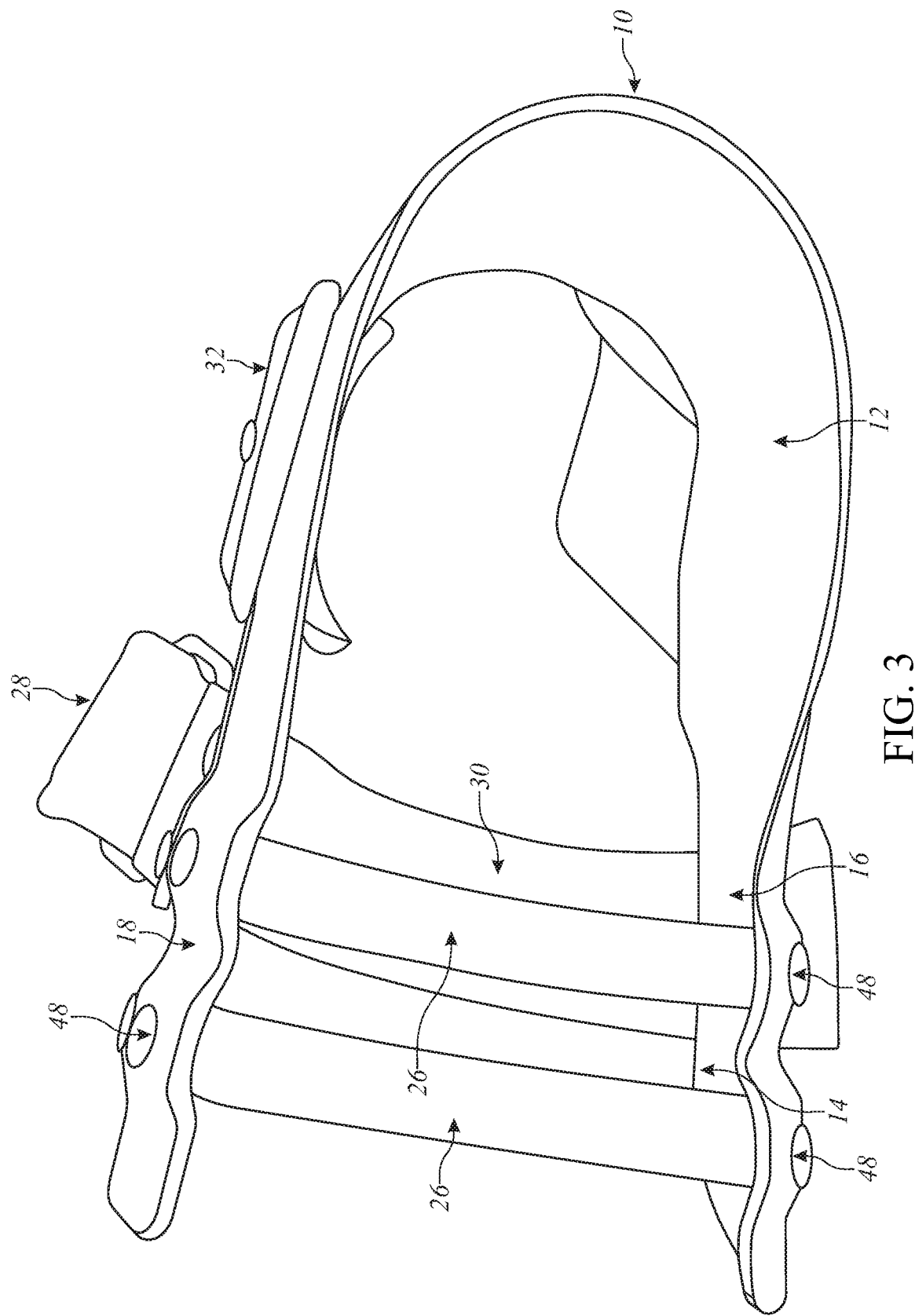
FIG. 3 is a perspective view showing the underside of the external ankle brace.

The rigid heel enclosure 10 has a rear portion 12 (FIG. 3), for receiving the heel of the shoe, and a forward portion 14, for surrounding the sides of the shoe. The heel enclosure 10 may be made from rigid plastic pieces or any other suitable material. The forward portion 14 further includes a medial sidewall 16 and a lateral sidewall 18. The rigid heel enclosure 10 also has an upper end 36 (FIG. 2) for receiving the upright extensions 20 and 22, and a lower end 38 for surrounding the bottom of the shoe.

Figure 4:
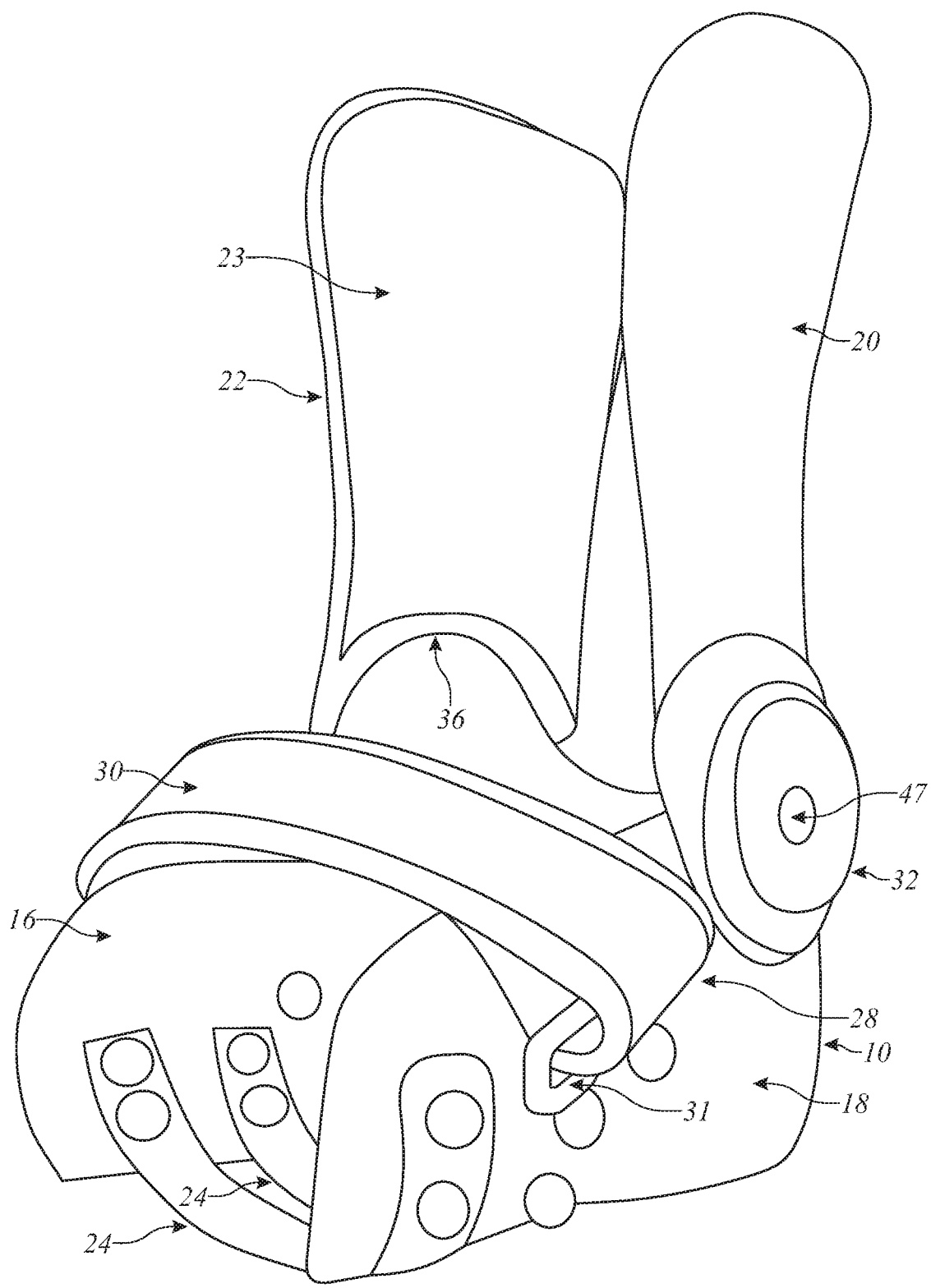
FIG. 4 is a perspective view of the external ankle brace from the lateral side.
Figure 5:
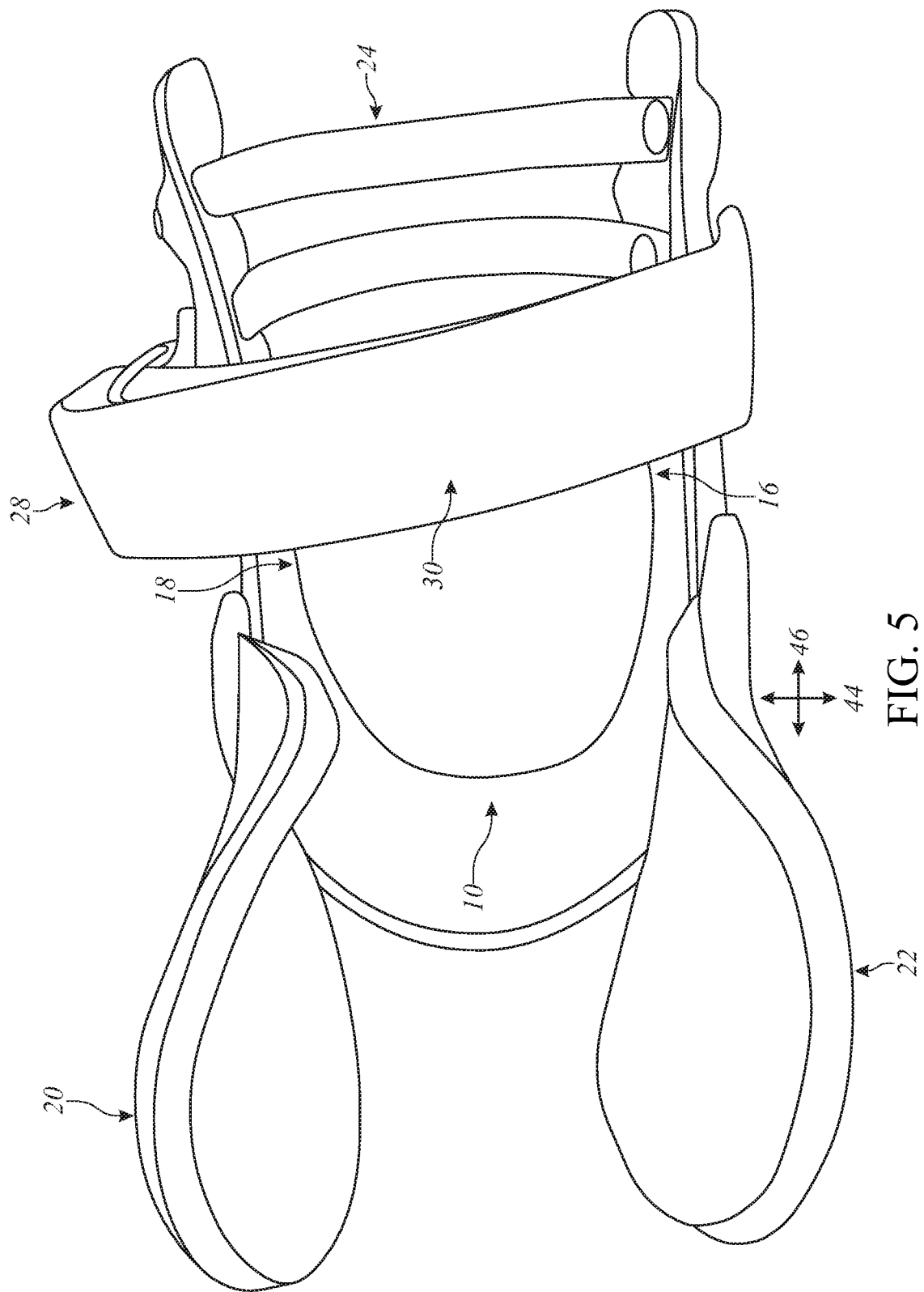
FIG. 5 is a top view of the external ankle brace.
Figure 6:
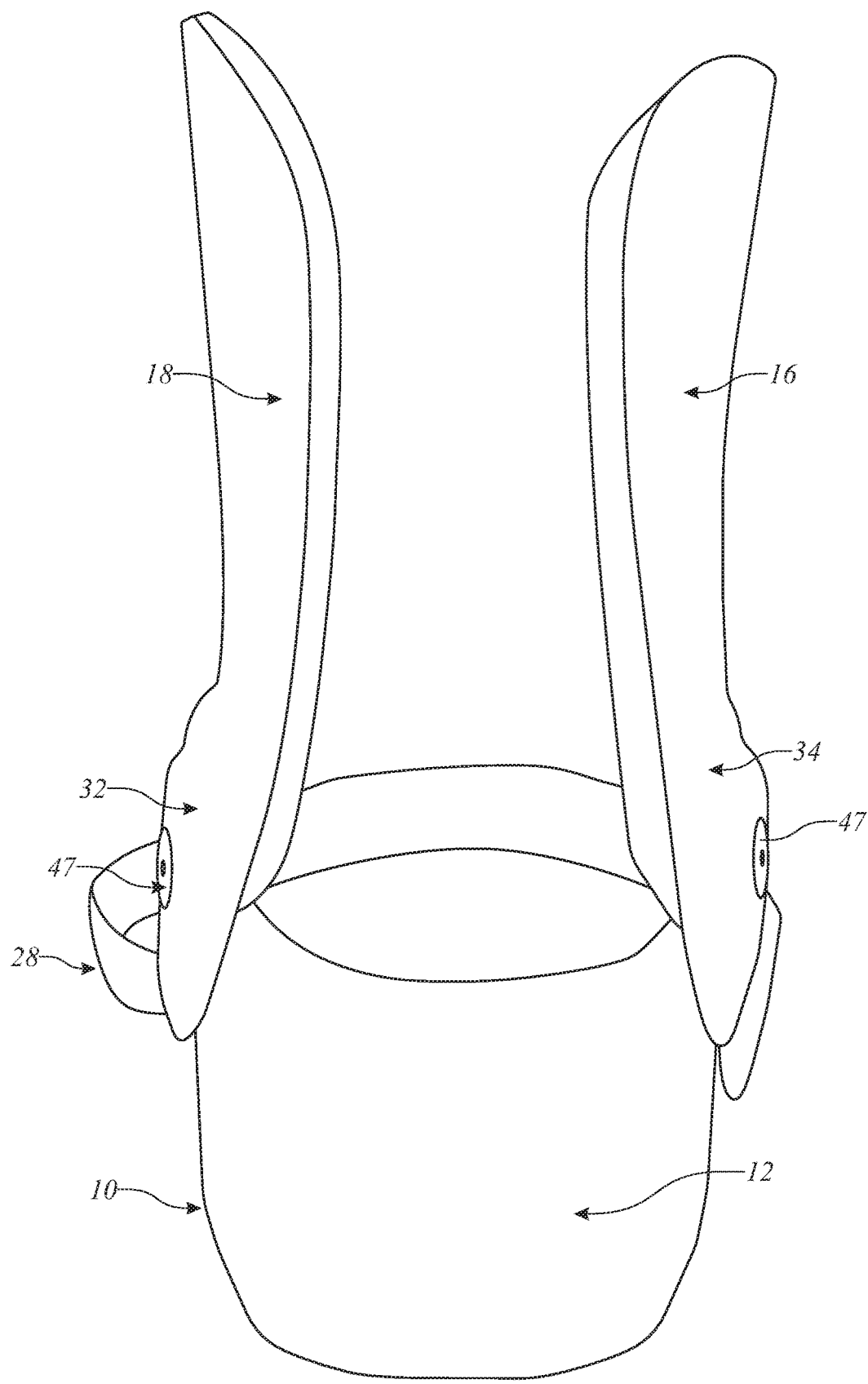
FIG. 6 is a rear view of the external ankle brace.

The lateral upright extension 20 is oriented generally perpendicular to at least the lateral sidewall 18 of the rigid heel enclosure 10 and is pivotally attached to the lateral sidewall 18 at the upper end 36 by a lateral ankle joint 32 (FIG. 4). The joint allows the lateral upright extension 20 to rotate during motion giving the external ankle brace a less restrictive feel compared to previous braces. The lateral upright extension 20 may be made from plastic or any other suitable material. The lateral ankle joint 32 includes a fastener 47 and allows the lateral upright extension 20 to rotate relative to the lateral sidewall 18. Although the current embodiment uses a screw as the fastener 47, one having ordinary skill in the art will appreciate that a pivot hinge, hex nut, revolving joint, or any other suitable member of the type commonly known in the art could be used to allow the joint to pivot. As shown in FIG. 5, the lateral upright extension 20 has a concave shape for increased comfort for the user. The lateral upright extension 20 can also include foam padding on the interior side 21 (FIG. 2) of the lateral upright extension 20 to increase comfort and to allow a better fit for the user.

The medial upright extension 22 is oriented generally perpendicular to at least the medial sidewall 16 of the rigid heel enclosure 10 and is pivotally attached to the medial sidewall 16 at the upper end 36 by a medial ankle joint 34. The medial upright extension 22 may be made of rigid plastic or any other suitable material. The medial ankle joint 34 has a fastener 47 and allows the medial upright extension 22 to rotate relative to the medial sidewall 16. To adjust for anatomical positioning of the ankle, the medial ankle joint 34 is positioned closer to the upper end 36 than the position of the lateral ankle joint 32. Although the current embodiment uses a screw as the fastener 47, one having ordinary skill in the art will appreciate that a pivot hinge, hex nut, revolving joint, or any other suitable member of the type commonly known in the art could be used to allow the joint to pivot. As shown in FIG. 5, the medial upright extension 22 has a concave shape for increased comfort for the user. The medial upright extension 22 can also include foam padding on the interior side 23 (FIG. 4) of the medial upright extension to increase comfort and to allow a better fit for the user.

The lower fastening system 24 has at least one connecting strap 26 and at least one strap fastener 48 for connecting the lateral sidewall 18 to the medial sidewall 16 (FIG. 2) while passing underneath the sole of the shoe. Although the current embodiment uses a rubber strap 26, one having ordinary skill in the art would appreciate that plastic, nylon, or any other suitable strap type that is commonly known in the art could be used. Similarly, although the current embodiment uses rivets 48 to fasten the straps to each of the lateral and medial sidewalls 18 and 16 respectively, any other fastener could be used.

The upper fastening system 28 has at least one connecting strap 30 for removably connecting the lateral sidewall 18 to the medial sidewall 16 while passing over the top of the shoe. The upper fastening system further includes a D-ring 31 which is fixed on the lateral sidewall. The hook and loop fastener strap 30 is fixed to the medial sidewall and is looped through the D-ring 31 and overlaps back onto the strap 30. The term "hook and loop fastener" is used herein to reference a type of fastening device such as, but not limited to, VELCRO® brand fasteners, available from Velcro USA Inc. & Velcro Group Corporation of Manchester, New Hampshire. This allows for an adjustable fastening system to accommodate various sizes without compromising support. Although the current embodiment uses a hook and loop fastener strap 30 to removeably connect the sidewalls 16 and 18, one having ordinary skill in the art would appreciate that any kind of removable and adjustable strap can be used. Similarly, although the current embodiment only uses one connecting strap 30, any number of straps can be used to removeably connect the sidewalls 16 and 18 over the top of the shoe.

As shown in FIG. 5, the external ankle brace 50 restricts movement of the ankle in the first directions indicated by arrows 44 and permits ankle movement in the second directions indicated by arrows 46.

Another embodiment could include an upright fastening system 40 (FIG. 1), which would have at least one connecting strap for removably connecting the lateral upright extension 20 to the medial upright extension 22 above the ankle. This connecting strap could be hook and loop fastener or any other type of strap that would allow for an adjustable and removable connection.

The innovation has been described in an illustrative manner. It is to be understood that the terminology, which has been used is intended to be in the nature of words of description rather than of limitation. Many modifications and variations of the invention are possible in light of the above teachings. Therefore, within the scope of the appended claims, the innovation may be practiced other than as specifically described.

In an embodiment, the upright fastening system comprises one connecting strap, the one connecting strap being the only connecting strap of the upright fastening system, the one connecting strap for removably connecting said lateral upright extension to said medial upright extension above the ankle. In an embodiment, the external ankle brace prevents inversion and eversion, the movement of the ankle in the first direction being inversion. In an embodiment, the external ankle brace permits dorsiflexion and plantar flexion, the movement of the ankle in the second direction being dorsiflexion. In an embodiment, the at least one connecting strap of the upper connecting system is connected, at locations forward of the lateral upright extension and medial upright extension, to portions of the lateral sidewall and of the medial sidewall which extend substantially longitudinally from the rear portion. In an embodiment, the rigid heel enclosure is a monolithic part. In an embodiment, the rigid heel enclosure consists of the rear portion, the medial sidewall and the lateral sidewall. In an embodiment, the connecting strap of the lower fastening system extends across the bottom of the sole of the shoe and upwards away from the sole of the shoe to respective locations proximate the oppositely disposed sides of the shoe forward of the talus of the wearer's foot. In an embodiment, the lateral ankle joint is located at a bottom portion of the lateral upright extension and at a top portion of the lateral sidewall. In an embodiment, the lateral ankle joint is located at a bottom portion of the lateral upright extension and at an upper end of the lateral sidewall. In an embodiment, the lateral sidewall extends towards the wearer's toe from a location where the at least one connecting strap of the upper fastening system connects to the lateral sidewall.

What is claimed is:

1. An external ankle brace, comprising:
a rigid heel enclosure having a rear portion and a forward portion, wherein
said rear portion is for receiving a heel portion of a shoe, the external ankle brace is configured to restrict movement of an ankle in a first direction and permit movement of the ankle in a second direction, wherein said external ankle brace is configured to be disposed on an exterior of the shoe and the shoe having the heel portion, a sole, a toe, a top, and oppositely disposed sides,
said forward portion includes a medial sidewall and a lateral sidewall for respective placement adjacent the oppositely disposed sides of the shoe, the medial and lateral sidewalls being cantilevered from the rear portion of the rigid heel enclosure, the medial and lateral sidewalls each being configured to extend away from the heel portion of the shoe in a longitudinal direction toward a wearer's toe and beyond a talus of the wearer's foot, each of the medial and lateral sidewalls being at least partially located adjacent to an instep area of a corresponding medial or lateral side of the shoe, and
the external ankle brace further comprises:
a lateral upright extension selectively perpendicular to at least the lateral sidewall of said rigid heel enclosure and pivotally attached to said lateral sidewall;
a medial upright extension selectively perpendicular to at least the medial sidewall of said rigid heel enclosure and pivotally attached to said medial sidewall;
a lower fastening system comprising at least one connecting strap for connecting said lateral sidewall to said medial sidewall underneath the sole of the shoe forward of the talus of the wearer's foot, the lower fastening system being configured so that when the external ankle brace is worn over the wearer's shoe, the lower fastening system does not extend over the top of the shoe in use, and the lower fastening system is the only structure connecting the lateral and medial sidewalls underneath the sole of the shoe such that a sole of the shoe underneath a heel of the wearer's foot is exposed to ambient space beneath the shoe; and
an upper fastening system comprising at least one connecting strap for connecting said lateral sidewall to said medial sidewall only across the top of the shoe.

2. The external ankle brace as set forth in claim 1, further including a lateral ankle joint that pivotally connects said lateral upright extension to said lateral sidewall and allows said lateral upright extension to move in the second direction relative to said rigid heel enclosure.

3. The external ankle brace as set forth in claim 2, wherein said lateral ankle joint in combination with said lateral upright extension and said rigid heel enclosure is configured to prevent movement of the ankle in the first direction.

4. The external ankle brace as set forth in claim 2, further including a medial ankle joint that pivotally connects said medial upright extension to said medial sidewall and allows said medial upright extension to move in the second direction relative to said rigid heel enclosure.

5. The external ankle brace as set forth in claim 4, wherein said medial ankle joint in combination with said medial upright extension and said rigid heel enclosure is configured to prevent movement in the first direction.

6. The external ankle brace as set forth in claim 4, wherein said rigid heel enclosure further includes oppositely disposed upper and lower ends, where said medial ankle joint is positioned closer to said upper end than the position of said lateral ankle joint.

7. The external ankle brace as set forth in claim 1, further comprising an upright fastening system comprising at least one connecting strap for removably connecting said lateral upright extension to said medial upright extension above the ankle, the at least one connecting strap of the upright fastening system extending in front of the shin of a wearer of the shoe when worn by the wearer.

8. The external ankle brace as set forth in claim 1, wherein at least one connecting strap of the upper fastening system is directly connected to portions of the lateral sidewall and of the medial sidewall which extend substantially longitudinally from the rear portion.

9. The external ankle brace as set forth in claim 3, further comprising an upright fastening system comprising at least one connecting strap for removably connecting said lateral upright extension to said medial upright extension above the ankle.

10. The external ankle brace as set forth in claim 3, further including a medial ankle joint that pivotally connects said medial upright extension to said medial sidewall and allows said medial upright extension to move in the second direction relative to said rigid heel enclosure.

11. The external ankle brace as set forth in claim 4, wherein said lateral ankle joint in combination with said lateral upright extension and said rigid heel enclosure and said medial ankle joint in combination with said medial upright extension and said rigid heel enclosure are configured to prevent movement in the first direction.

12. The external ankle brace as set forth in claim 1, wherein the at least one connecting strap of the upper fastening system is for removably connecting the lateral sidewall to the medial sidewall across the top of the shoe.

13. The external ankle brace as set forth in claim 1, wherein the shoe is located in the external ankle brace, and the shoe is a cleated shoe.

14. The external ankle brace as set forth in claim 1, further comprising an upright fastening system comprising two separate connecting straps for removably connecting said lateral upright extension to said medial upright extension above the ankle.

15. The external ankle brace as set forth in claim 1, wherein the at least one connecting strap for connecting said lateral sidewall to said medial sidewall underneath the sole of the shoe comprises two connecting straps for connecting said lateral sidewall to said medial sidewall underneath the sole of the shoe.

16. The external ankle brace as set forth in claim 1, wherein the shoe is an athletic shoe.

17. The external ankle brace as set forth in claim 1, further comprising an upright fastening system comprising one connecting strap, the one connecting strap being the only connecting strap of the upright fastening system, the one connecting strap for removably connecting said lateral upright extension to said medial upright extension above the ankle.

18. The external ankle brace as set forth in claim 4, wherein the external ankle brace prevents inversion and eversion, the movement of the ankle in the first direction being inversion.

19. The external ankle brace as set forth in claim 4, wherein the external ankle brace permits dorsiflexion and plantar flexion, the movement of the ankle in the second direction being dorsiflexion.

20. The external ankle brace as set forth in claim 1, wherein the at least one connecting strap of the upper fastening system is connected, at locations forward of the lateral upright extension and medial upright extension, to portions of the lateral sidewall and of the medial sidewall which extend substantially longitudinally from the rear portion.

21. The external ankle brace of claim 1, wherein the at least one connecting strap of the upper fastening system is for removably connecting said lateral sidewall to said medial sidewall, and wherein the external ankle brace is configured so that the at least one connecting strap of the upper fastening system extends across the top of the shoe forward of the talus of the wearer's foot when the external ankle brace is worn by the wearer.

22. The external ankle brace as set forth in claim 1, wherein the rigid heel enclosure is a monolithic part.

23. The external ankle brace as set forth in claim 1, wherein the lateral upright extension is oriented perpendicular to at least the lateral sidewall and is pivotally attached to the lateral sidewall at an upper end of the lateral sidewall by a lateral ankle joint.

24. The external ankle brace as set forth in claim 1, wherein the lateral upright extension is pivotally attached to the lateral sidewall at an upper end of the lateral sidewall by a lateral ankle joint.

25. The external ankle brace as set forth in claim 1, wherein the medial upright extension is made from plastic and the lateral upright extension is made from plastic.

26. The external ankle brace as set forth in claim 1, wherein the rigid heel enclosure is made from plastic.

27. The external ankle brace as set forth in claim 1, wherein the rigid heel enclosure consists of the rear portion, the medial sidewall and the lateral sidewall.

28. The external ankle brace of claim 1, wherein the external ankle brace is configured so that the at least one connecting strap of the lower fastening system extends across the bottom of the sole of the shoe and upwards away from the sole of the shoe to respective locations proximate the oppositely disposed sides of the shoe forward of the talus of the wearer's foot when the external ankle brace is worn by the wearer.

29. The external ankle brace as set forth in claim 2, wherein said lateral ankle joint is located at a bottom portion of the lateral upright extension and at a top portion of the lateral sidewall.

30. The external ankle brace as set forth in claim 2, wherein said lateral ankle joint is located at a bottom portion of the lateral upright extension and at an upper end of the lateral sidewall.

31. The external ankle brace of claim 1, wherein the lateral sidewall extends towards the wearer's toe from a location where the at least one connecting strap of the upper fastening system connects to the lateral sidewall.

\* \* \* \* \*